United States Patent [19]

Pitchford

[11] 4,425,339
[45] Jan. 10, 1984

[54] TREATMENT OF MENOPAUSAL SYMPTOMS

[75] Inventor: Alan G. Pitchford, Berkshire, England

[73] Assignee: Syntex (U.S.A.) Inc., Palo Alto, Calif.

[21] Appl. No.: 252,518

[22] Filed: Apr. 9, 1981

[51] Int. Cl.³ ............................................. A61K 31/56
[52] U.S. Cl. .................... 424/239; 206/44 R
[58] Field of Search ................. 424/238, 239; 206/42

[56] References Cited

U.S. PATENT DOCUMENTS

| | | | |
|---|---|---|---|
| 3,568,828 | 3/1971 | Lerner | 424/238 |
| 3,608,075 | 9/1971 | Glen | 424/238 |
| 3,932,635 | 1/1976 | Segre | 424/239 |
| 3,957,982 | 5/1976 | Lachnit-Fixson et al. | 424/239 |
| 4,145,416 | 3/1979 | Lachnit-Fixson et al. | 424/238 |
| 4,145,416 | 3/1979 | Lachnit-Fixson et al. | 424/239 |

*Primary Examiner*—Elbert L. Roberts
*Attorney, Agent, or Firm*—Tom M. Moran; Alan M. Krubiner

[57] ABSTRACT

A method for treating menopausal symptoms and a pharmaceutical package for effecting the method are disclosed. The method comprises a three phase sequence of estrogen and progestogen administration and an additional drug-free fourth phase during at least one menstrual cycle as follows:

(a) as phase one, 0.2 mg to 1.5 mg of estrone, (or of other natural estrogen in an amount sufficient to result in an effect equivalent to the selected amount of estrone within the aforegiven range) for 4-9 days, followed by (b) as phase two, 0.2 mg to 1.5 mg of estrone, (or of other natural estrogen in an amount sufficient to result in an effect equivalent to the selected amount of estrone within the aforegiven range), plus 0.2 to 1.5 mg of norethisterone (or of other styptic progestogen, in an amount sufficient to result in an effect equivalent to the selected amount of norethisterone within the aforegiven range); with the proviso that the dosage levels of estrogen and progestogen be approximately equal (as defined in terms of estrone and nonethisterone above); for 6-11 days, followed by (c) as phase three, twice the dosage of estrogen and twice the dosage of progestogen used in phase two, for at least 6 days, or for an arbitrarily selected greater number of days to a maximum of 90 days; followed by (d) as phase four, no therapeutically active dosage, i.e., either no treatment or a placebo, for 6-8 days.

14 Claims, 2 Drawing Figures

TREATMENT OF MENOPAUSAL SYMPTOMS

BACKGROUND OF THE INVENTION

The present invention relates to novel methods and articles of manufacture which are packages containing compositions useful for treating symptoms associated with the menopause. More particularly, the present invention is directed to relieving or preventing menopausal or perimenopausal symptoms in the female human by use of a stepwise, graded, sequential, natural estrogen-progestogen regimen.

Treatment of the menopause has been focused largely on the distressing symptoms associated therewith, e.g., hot flushes (or flashes), headache, insomnia, fatigue, nervousness, depression, joint pains, and so forth.

More serious symptoms are recurrent cysto-urethritis; dysparunia and vaginal atrophy; and menorrhagia. Perhaps the most serious associated biological change is osteoporosis, a process which begins during menopause and continues in the post-menopausal years. This bone-degeneration is gradual, but irreversible; hip fractures, which are associated with substantial mortality risk, are common among post-menopausal women.

The administration of female hormones has been recommended since the menopause can be regarded as a deficiency state with respect to the production of those hormones. Estrogens, both synthetic and natural, have been used. Some efforts to replace both types of deficient hormones, namely, estrogen and progestogen, have relied on the commonly available oral contraceptive regimens. These regimens do not approach the physiological estrogen and progestogen levels of the natural ovarian cycle, since they are directed to disrupting it and may be responsible for some intolerance of the treatment because of relative excesses of the components.

Attempts to mimic the natural level of hormones in the cycle by administration of estrogen and/or progestogen in amounts presumably necessary to restore the hormonal concentrations to premenopausal levels are well known, (See, e.g., U.S. Pat. No. 3,733,407). Several regimens are, in fact, marketed, e.g., Cyclo-Progynova, (Schering); Premarin (Ayerst) and Prempak (Ayerst).

The present invention, provides a "rest" period wherein no hormones are administered, requires the use of natural, rather than synthetic, estrogen, and includes the use of a styptic progestogen, e.g., norethisterone, and thus avoids the problems associated with constant dosage and synthetic materials.

SUMMARY OF THE INVENTION

The present invention relates to a method for treating menopausal symptoms in the female human, which method comprises administering to a subject in need of such treatment a daily sequence of unit dosages over a repeating cycle, which dosage sequence comprises
  (a) administering, as phase one, about 0.2 mg to 1.5 mg of estrone, (or of other natural estrogen in an amount sufficient to result in an effect equivalent to the selected amount of estrone within the aforegiven range) for 4–9 days, followed by
  (b) administering, as phase two, about 0.2 mg to 1.5 mg of estrone, (or of other natural estrogen in an amount sufficient to result in an effect equivalent to the selected amount of estrone within the aforegiven range), plus about 0.2 to 1.5 mg of norethisterone (or of other styptic progestogen, in an amount sufficient to result in an effect equivalent to the selected amount of nonethisterone within the aforegiven range); with the proviso that the dosage levels of estrogen and progestogen be approximately equal (as defined in terms of estrone and nonethisterone above); for 6–11 days, followed by
  (c) administering, as phase three, twice the dosage of estrogen and twice the dosage of progestogen used in phase two, for 6 days, or for an arbitrarily selected greater number of days as individually desired to a maximum of 90 days; followed by
  (d) administering, as phase four, no therapeutically active dosage, i.e., either no treatment or a placebo, for 6–8 days.

Another aspect of the invention relates to pharmaceutical packages designed to effectuate the aforesaid method.

DETAILED DESCRIPTION

Definitions:

As used herein:

"Treating" refers to subjecting an individual to a specified regimen for the purpose of relieving symptom, or preventing, or palliating any specified condition. Thus "treating menopausal symptoms" refers both to relieving symptoms already present and to preventing symptoms from occurring, as well as to palliating the subject's response to said symptoms.

The term "menopause" is herein synonymous with perimenopause and refers to the events leading to and associated with the cessation of menstruation in the human female, whether naturally or artificially occurring, i.e., the climacteric. Commonly this state begins between the ages of 40 to 50 in the human female, and may continue for weeks to months or even years thereafter.

The "symptoms" associated with the menopause and the perimenopause interval are inclusive of hot flushes, nervousness, depression, and so forth, and other, perhaps resultant, conditions such as atherosclerosis and osteoporosis.

"Menstrual cycle" or "cycle" refers to the well known and repetitively occurring menstrual sequence in the premenopausal female, of 28 days typical duration.

"Day one" of said cycle is defined as the first day of menstruation, and the days are numbered sequentially thereafter until menstruation again occurs; normally 28 days in number, but in some cases slightly more or less.

The "natural estrogen" as herein described can be selected from any of those materials commonly known as and referred to as estrogenic agents which are produced during the menstrual cycle of premenopausal female humans or which occur in other animals or plants. Natural estrogens include, e.g., estrone, estradiol, and estriol.

"Styptic progestogens" are those progestogens which result in a reduction of the amount of menstrual flow. Those useful in the present invention include e.g., norethisterone, lynestranol, and norethisterone acetate.

"Approximately equal" means that the percent difference between two amounts is 10% or less. "Twice" or "two-times" includes this same percentage discrepancy.

Formulation, Sequence and Preferred Embodiments

Figure 1:
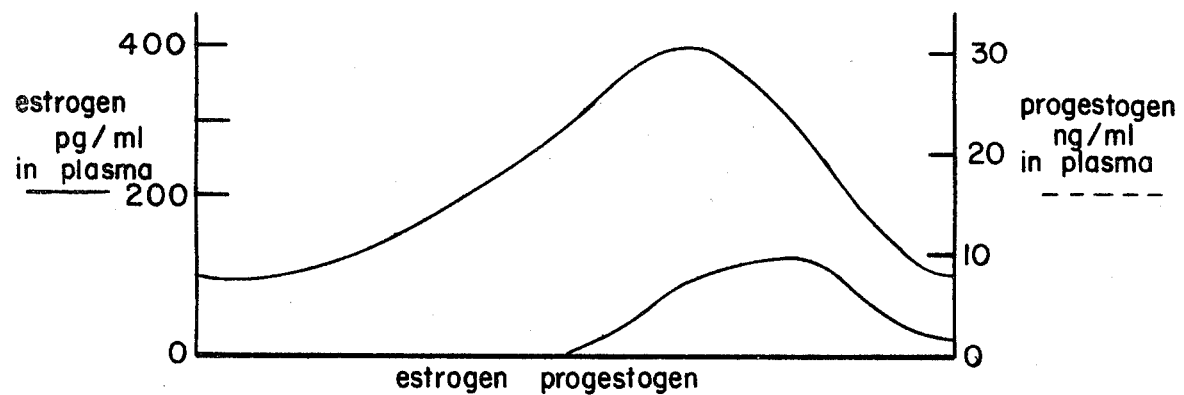
Figure 2:
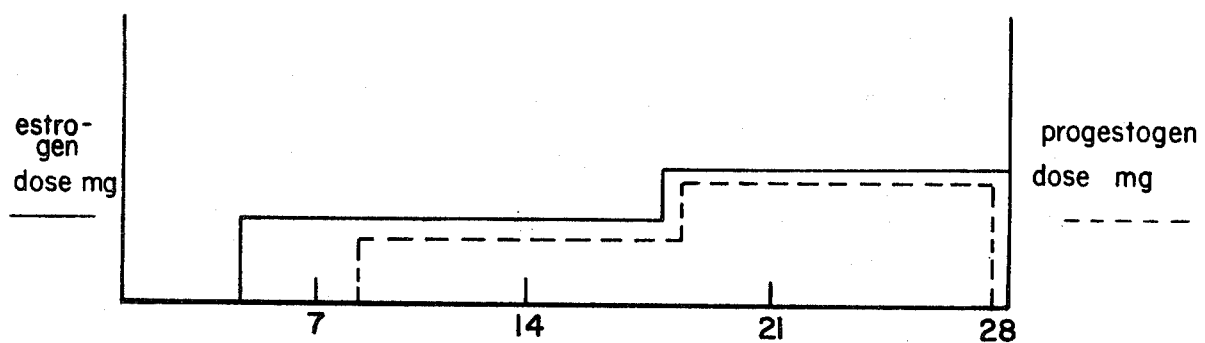

FIGS. 1 and 2 show the pattern contrast between the "natural" cycle, and the treatment of the invention herein. FIG. 1 shows plasma hormone levels of estrogen and progestogen in the premenopausal female. It is seen that estrogen levels are maintained at at least about 100 pg/per ml plasma throughout the cycle, and are maximal at about day 14. Progestogen levels, however, are maximized at approximately day 21. FIG. 2 shows a high and low dosage level of the invention herein. In each case estrogen and progestogen are administered in stepwise fashion and estrogen is maintained at high levels while progestrogen is increased.

The timing of the sequence of administration of phase one through phase four is controlled by the consideration of a number of factors. The menstrual cycle itself is of course, controlled by the hormone levels attributable to both the subject's natural secretion and to the administered dosages. Therefore, an attempt should be made to synchronize the administration sequence with the secretion sequence in those subjects who are maintaining at least some menstrual periods. In order to do this, phase one would preferably commence on day 5 of the subject's menstrual period. Of course, if the subject is not menstruating at all, phase one is begun at any arbitrary time; but as the dosage-induced cycle is established, phase one of the succeeding treatment would preferably begin on day 5 of the externally imposed cycle.

Since the normal cycle is 28 days, a preferred timing of the sequence would ordinarily aim for a repeating cycle of that length. In order to do this a preferable duration of phase one is 5 days; of phase two, 7 days; of phase three, 9 days; and of phase four, 7 days. Menstruation would begin, then, between the second and the fourth day of phase four. As noted above, however, acceptable ranges for phases one and two are 4-9 days and 6-11 days, respectively, these constraints being necesary to secure the efficacy of the treatment. However, phase three may be prolonged, more or less indefinitely—i.e., up to about three months—because menstruation will not again occur until the progestogen levels decrease. Approximately three to four days after phase three is terminated, and phase four is commenced, menstruation will occur. If the subject is to continue treatment, phase one would again be resumed on day 5 of the cycle (i.e., about 8 days after the beginning of phase four. If treatment is dropped, and then again resumed, the considerations noted above apply.

It is preferable, both for psychological and physiological reasons that phase three not be prolonged. Thus, in the most preferred embodiment of the invention, phase one is 5 days; phase two 7 days, phase three 9 days, phase four 7 days.

The method of the present invention is conventionally practiced by oral administration of the graded sequential components, in a suitable admixture with a pharmaceutically acceptable non-toxic carrier. Thus, the components can be appropriately compounded in any pharmaceutically acceptable non-toxic form and can be packaged in any system convenient for proper delivery. For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 0.1-95% active ingredient, preferably 1.0-70%. See *Remington's Pharmaceutical Sciences,* Mack Publishing Co., Easton, Pa., 15th Edition, 1975, especially Chapter 87. Dispensing systems useful herein include those which accommodate to conventional packaging equipment, such as transparent strip foil packages contiguously arranged in daily doses or other conventional means known in the art.

A preferred estrogen is estrone, and a preferred progestogen is norethisterone.

Subjects who are still menstruating and/or are secreting hormones of their own will require less dosage than those whose hormone levels are greatly depressed. Also, it is frequently found that after initial administration, smaller doses are required to maintain a satisfactory result—hence a reduced "maintenance" schedule is indicated.

Therefore for ease of formulation and prescription a low dose regimen and a high dose regimen containing specific amounts of hormone are preferred; as described below:

|  | Low dose regimen | High dose regimen |
| --- | --- | --- |
| Stage 1 (4-9 days) | 0.4-0.6 mg estrone | 0.9-1.1 mg estrone |
| Stage 2 (6-11 days) | 0.4-0.6 mg estrone | 0.9-1.1 mg estrone |
|  | 0.4-0.6 mg norethisterone | 0.9-1.1 mg norethisterone |
| Stage 3 (6-90 days) | 0.8-1.2 mg estrone | 1.8-2.2 mg estrone |
|  | 0.8-1.2 mg norethisterone | 1.8-2.2 mg norethisterone |
| Stage 4 (6-8 days) | no hormones | no hormones |

In the most preferred embodiment,

Stage 1 comprises 5 days (day 4–day 8);
Stage 2 comprises 7 days (day 9–day 15);
Stage 3 comprises 9 days (day 16–day 24);
Stage 4 comprises 7 days (day 25–day 3 of the succeeding cycle).

The following examples serve to illustrate the invention and are not intended to limit it.

EXAMPLE 1

Compositions of Unit Dosage for a 28-day cycle:
The following exemplifies the contents of tablets to be contained in a single package for administration during one 28-day cycle:

| Day No. 4–8: Stage One - 5 tablets | |
| --- | --- |
| 0.50 mg | estrone, ultramicronized to average 3μ particle size |
| 33.50 mg | lactose |
| 17.20 mg | cornstarch |
| 2.10 mg | polyvinylpyrrolidone |
| 1.70 mg | talc |
| 55.00 mg | total weight which is supplemented to about 90 mg with a customary sugar mixture |

| Day No. 9–15: Stage Two - 7 tablets | |
| --- | --- |
| 0.50 mg | estrone, ultramicronized to average 3μ particle size |
| 0.50 mg | norethisterone |
| 33.00 mg | lactose |
| 17.20 mg | cornstarch |

| Day No. 9–15: Stage Two - 7 tablets | |
| --- | --- |
| 2.10 mg | polyvinylpyrrolidone |
| 1.70 mg | talc |
| 55.00 mg | total weight which is supplemented to about 90 mg with a customary sugar mixture |

| Day No. 16–24: Stage Three - 9 tablets | |
| --- | --- |
| 1.0 mg | estrone, ultramicronized to average 3μ particle size |
| 1.0 mg | norethisterone |
| 32.50 mg | lactose |
| 17.20 mg | cornstarch |
| 2.10 mg | polyvinylpyrrolidone |
| 1.70 mg | talc |
| 55.00 mg | total weight which is supplemented to about 90 mg with a customary sugar mixture |

| Day No. 25–28 [Day 1–3 (of subsequent cycle)]: Stage Four - 7 tablets | |
| --- | --- |
| 34.0 mg | lactose |
| 17.20 mg | cornstarch |
| 2.10 mg | polyvinylpyrrolidone |
| 1.70 mg | talc |
| 55.00 mg | total weight which is supplemented to about 90 mg with a customary sugar mixture |

EXAMPLE 2

Sample package and insert (directions) for the Composition regime of Example 1.

The following packaging design and instructions is appropriate to the composition set of Example 1:

| INSIDE | OUTSIDE |
| --- | --- |
| (About these tablets) (Fold) | (Display) (Fold) |
| (How to use this pack) (Fold) | (Blank) (Fold) |
| —(Flap out)—(Cut) (APPROX. 8 mm. HOLES SHOWING FOIL BACKING). | —(Flap out)— (Printed tablet order). (APPROX. 8 mm. HOLES SHOWING COLORED TABLETS THROUGH CLEAR BUBBLE). |
| + + | 1 2 3 4 5 6 7   Day of Cycle |
| + + + + + + | 1 2 3   Pill No. |
| + + + + + + | 8 9 10 11 12 13 14   Day of Cycle |
| + + + + + | 4 5 6 7 8 9 10   Pill No. |
| | 15 16 17 18 19 20 21   Day of Cycle |
| | 11 12 13 14 15 16 17   Pill No. |
| | 22 23 24 25 26 27 28   Day of Cycle |
| | 18 19 20 21 22 23 24   Pill No. |
| | 1 2 3 4 5 6 7   Day of Cycle |
| | 25 26 27 28   Pill No. |

ABOUT THESE TABLETS (The tablet set herein) is used to control menopausal symptoms. It is not a birth control pill and will not prevent pregnancy.

Oral contraceptives should not be taken at the same time as these tablets and, if necessary, you should therefore ask your doctor about alternative means of mechanical protection.

When treatment is first started, tingling of the breasts, slight nausea or occasional vaginal bleeding may occur—this should settle after a short time.

If you have any unusual symptoms, contact your doctor.

To be taken under medical supervision.

HOW TO USE THIS PACK

IF YOU ARE MENSTRUATING REGULARLY take tablet No. 1 on the 5th day of your menstrual period. IF YOU ARE MENSTRUATING IRREGULARLY OR NOT AT ALL take the first tablet on a day suitable to yourself.

Continue to take one tablet each day following the numerical order. Make a habit of taking your tablet at the same time of day (such as before going to bed).

Try not to forget a tablet. If your forget your tablets on one or more days, discard the missed tablets and resume your course of therapy on the appropriate day.

While taking (the tablet set herein) you should get a regular withdrawal bleeding the next day after tablet No. 24 each month. However, even if you do not get bleeding you should re-start your treatment the next day after tablet No. 28.

Alternatively, these instructions may be printed as a leaflet, and the package instructions modified as follows.

| TRADEMARK |
| --- |
| Before commencing treatment please read the enclosed instruction leaflet carefully. If you have any difficulties following the instructions, please ask your doctor for assistance. |
| DIRECTIONS |
| To remove a tablet, press firmly with your thumb on the appropriate clear plastic bubble. This may be helped by holding the card so that your other fingers surround the aluminum foil through which the tablet will emerge. |

What is claimed is:

1. A method for treating menopausal symptoms in the female human, which method comprises administering to a subject in need of such treatment, a daily sequence of unit dosages over a repeating cycle, which dosage sequence comprises:

(a) administering, as phase one, for a period of 4–9 days, a natural estrogen in daily dosages corresponding in estrogenic activity to about 0.2–1.5 mg of estrone, followed by (b) administering, as phase two, for a period of 6–11 days, daily dosages of a combination of a natural estrogen and a styptic progestogen, wherein the amounts of estrogen and progestogen are approximately equal by weight and correspond in estrogenic activity to about 0.2–1.5 mg of estrone, and in progestogenic activity to about 0.2–1.5 mg of norethisterone, followed by (c) administering, as phase three, for a period of 6–90 days, a combination of a natural estrogen and a styptic progestogen in daily dosages twice those administered in phase two, followed by (d) administering, as phase four, no therapeutically active dosage, i.e., either no treatment or a placebo, for 6-8 days.

2. The method of claim 1 wherein the period specified in (a) is 5 days;
the period specified in (b) is 7 days;
the period specified in (c) is 9 days;
the period specified in (d) is 7 days.

3. The method of claim 2, wherein:
the dosage in (a) of natural estrogen corresponds in estrogenic activity to about 0.4-0.6 mg of estrone;
the dosages in (b) of natural estrogen and styptic progestogen correspond in estrogenic activity to about 0.4-0.6 mg of estrone, and in progestogenic activity to about 0.4-0.6 mg of norethisterone;
the dosages in (c) of natural estrogen and styptic progestogen are each twice the amount of the corresponding hormone in (b), and correspond in estrogenic activity to about 0.8-1.2 mg of estrone, and in progestogenic activity to about 0.8-1.2 mg of norethisterone.

4. The method of claim 2, wherein:
the dosage in (a) of natural estrogen corresponds in estrogenic activity to about 0.9-1.1 mg of estrone;
the dosages in (b) of natural estrogen and styptic progestogen correspond in estrogenic activity to about 0.9-1.1. mg of estrone, and in progestogenic activity to about 0.9-1.1 mg of norethisterone;
the dosages in (c) of natural estrogen and styptic progestogen are each twice the amount of the corresponding hormone in (b) and correspond in estrogenic activity to about 1.8-2.2 mg of estrone, and in progestogenic activity to about 1.8-2.2 mg of norethisterone.

5. The method of claim 3 or claim 4 wherein the natural estrogen is estrone.

6. The method of claim 3 or claim 4 wherein the progestrogen is norethisterone.

7. The method of claim 3 or claim 4 wherein the natural estrogen is estrone and the progestogen is norethisterone.

8. A pharmaceutical composition for treating menopausal symptoms in the human female which comprises:
(a) 4-6 dosage units each containing, in admixture with a pharmaceutically acceptable excipient, a natural estrogen in an amount corresponding in estrogenic activity to about 0.2 mg to 1.5 mg of estrone; and
(b) 6-11 dosage units, each containing, in admixture with a pharmaceutically acceptable excipient, a combination of a natural estrogen and a styptic progestogen, wherein the amounts of estrogen and progestogen are approximately equal by weight and correspond in estrogenic activity to about 0.2 to 1.5 mg of estrone, and in progestogenic activity to about 0.2 to 1.5 mg of norethisterone; and
(c) 6-90 dosage units each containing, in admixture with a pharmaceutically acceptable excipient, twice the amount of estrone and twice the amount of progestogen as in (b); and optionally
(d) 6-8 dosage units containing no estrogen or progestogen but only a pharmaceutically acceptable placebo.

9. The pharmaceutical composition of claim 8, wherein
the number of dosage units in (a) is 5;
the number of dosage units in (b) is 7;
the number of dosage units in (c) is 9;
the number of dosage units in (d) is 7.

10. The pharmaceutical composition of claim 8, wherein
the dosage in (a) of natural estrogen corresponds in estrogenic activity to about 0.4-0.6 mg of estrone;
the dosages in (b) of natural estrogen and styptic progestogen correspond in estrogenic activity to about 0.4-0.6 mg of estrone and in progestogenic activity to about 0.4-0.6 mg of norethisterone;
the dosages in (c) of natural estrogen and styptic progestogen are each twice the amount of the corresponding hormone in (b) and correspond in estrogenic activity to about 0.8-1.2 mg of estrone and in progestogenic activity to about 0.8-1.2 mg of norethisterone.

11. The pharmaceutical composition of claim 8, wherein
the dosage in (a) of natural estrogen corresponds in estrogenic activity to about 0.9-1.1 mg of estrone;
the dosages in (b) of natural estrogen and styptic progestogen correspond in estrogenic activity to about 0.9-1.1 mg of estrone and in progestogenic activity to about 0.9-1.1 mg of norethisterone,
the dosages in (c) of natural estrogen and styptic progestogen are each twice the amount of the corresponding hormone in (b) and correspond in estrogenic activity to about 1.8-2.2 mg of estrone and in progestogenic activity to about 1.8-2.2 mg of norethisterone.

12. The pharmaceutical composition of claim 10 or 11, wherein the natural estrogen is estrone.

13. The pharmaceutical composition of claim 10 or 11, wherein the styptic progestogen is norethisterone.

14. The pharmaceutical composition of claim 10 or 11, wherein the natural estrogen is estrone and the styptic progestogen is norethisterone.

* * * * *